(12) United States Patent
Castillo et al.

(10) Patent No.: US 12,036,549 B2
(45) Date of Patent: Jul. 16, 2024

(54) SYSTEM FOR THE PRODUCTION OF CELLS AND/OR CELL PRODUCTS

(71) Applicant: UNIVERCELLS TECHNOLOGIES S.A., Nivelles (BE)

(72) Inventors: José Castillo, Brussels (BE); Bastien Mairesse, Uccle (BE)

(73) Assignee: UNIVERCELLS TECHNOLOGIES S.A., Nivelles (BE)

( * ) Notice: Subject to any disclaimer, the term of this patent is extended or adjusted under 35 U.S.C. 154(b) by 838 days.

(21) Appl. No.: 16/347,961

(22) PCT Filed: Nov. 8, 2017

(86) PCT No.: PCT/EP2017/078613
§ 371 (c)(1),
(2) Date: May 7, 2019

(87) PCT Pub. No.: WO2018/087150
PCT Pub. Date: May 17, 2018

(65) Prior Publication Data
US 2019/0275519 A1   Sep. 12, 2019

(30) Foreign Application Priority Data

Nov. 8, 2016  (BE) .................. 2016/5838

(51) Int. Cl.
*C12M 1/00*   (2006.01)
*B01L 1/04*   (2006.01)
(Continued)

(52) U.S. Cl.
CPC ........... *B01L 3/502715* (2013.01); *B01L 1/04* (2013.01); *C12M 23/52* (2013.01); *C12M 37/00* (2013.01); *C12N 7/00* (2013.01); *B01L 2300/06* (2013.01)

(58) Field of Classification Search
CPC ........ C12M 23/52; A61L 2202/25; A61L 2/24
See application file for complete search history.

(56) References Cited

U.S. PATENT DOCUMENTS 5,656,491 A * 8/1997 Cassani .................. C12M 23/52
435/289.1
7,985,382 B1   7/2011 Henry et al.
(Continued)

FOREIGN PATENT DOCUMENTS

EP      0670889 B1   8/1998
JP   2005013094 A   1/2005
(Continued)

OTHER PUBLICATIONS

English Translation Abstract for RU139934U1 dated Apr. 27, 2014.
English Translation Abstract for RU98369U1 dated Oct. 20, 2010.

*Primary Examiner* — Jonathan M Hurst
(74) *Attorney, Agent, or Firm* — Dickinson Wright PLLC; Andrew D. Dorisio

(57) ABSTRACT

The invention provides a method and a system for the production of viruses or virus derived products. The system comprises a containment enclosure provided with a single entry means and a single exit means which are movable between a closed position and an open position. The containment enclosure comprises at least one production unit comprising at least one bioreactor for culturing the virus, said bioreactor is provided with at least one inlet and at least one outlet; at least one purification unit fluidly connected to the production unit and comprising at least one purification means having at least one inlet and at least one outlet. The system further comprises at least one inactivation and/or at least one gas decontamination unit. The containment enclosure comprises at least one process control device connected
(Continued)

to the exit means. The movement of the exit means from the closed position to the open position is controllable by said process control device.

16 Claims, 3 Drawing Sheets

(51) Int. Cl.
  *B01L 3/00* (2006.01)
  *C12M 1/12* (2006.01)
  *C12N 7/00* (2006.01)

(56) References Cited

U.S. PATENT DOCUMENTS

| 2005/0193643 | A1 | 9/2005 | Pettus |
| 2009/0126285 | A1 | 5/2009 | Suh et al. |
| 2013/0109291 | A1 | 5/2013 | Holtz et al. |
| 2015/0159127 | A1* | 6/2015 | Guerini ................. C12M 41/48 435/71.1 |
| 2015/0258233 | A1* | 9/2015 | Brown ....................... A61L 2/24 422/292 |
| 2016/0128886 | A1* | 5/2016 | Merino ..................... E04H 3/08 600/21 |

FOREIGN PATENT DOCUMENTS

| JP | 2006223207 A | 8/2006 |
| JP | 4632806 B2 | 2/2011 |
| JP | 2016510981 A | 4/2016 |
| KR | 2015-0125714 A | 11/2015 |
| RU | 98369 U1 | 10/2010 |
| RU | 139934 U1 | 4/2014 |
| WO | WO2014049151 A1 | 4/2014 |
| WO | WO2016128361 A1 | 8/2016 |

* cited by examiner

SYSTEM FOR THE PRODUCTION OF CELLS AND/OR CELL PRODUCTS

TECHNICAL FIELD

The invention pertains to a system and a method for the contained and confined production of biologics. In particular, the invention pertains to the production of cells, viruses or cells- or virus-derived products.

BACKGROUND

Biopharmaceuticals and renewable chemicals (also referred to herein as "biologics") are a growing segment in the global biologics market. Known biologics can include, for example, veterinary proteins, human proteins, animal proteins, plant proteins, pharmaceutical proteins, microbial biomass, viruses or virus particles. Biologics manufacturing is a technologically complicated process which is highly regulated. Said manufacturing requires bioreactor capabilities which can produce biologics compatible with good laboratory practice or good manufacturing practice standards. In comparison to other types of manufacturing, biologics require far more planning, investment, documentation, skilled personnel, and regulatory approval, and therefore can be much riskier.

Research and manipulation of certain viruses require specific containment levels provided by known bio-safety level 3 (BSL-3) and bio-safety level 4 (BSL-4) facilities. These facilities are expensive, require substantial training for the personnel involved and require the use of protective clothing and equipment. Providing existing facilities with means preventing contamination of the outer environment by the cultured cells or viruses results in extremely high capital expenditure.

It is the aim of the current invention to provide methods and systems for the production of viruses or virus products which overcome at least part of the above mentioned drawbacks and disadvantages. One object of the invention is to provide methods and systems which allow the production of viruses or virus products and eliminate any risk of environment contamination by the produced virus.

SUMMARY OF THE INVENTION

In a first aspect, the present invention provides a system for the production of cells, viruses or cells- or virus-derived products, according to claim 1.

The system preferably comprises a containment enclosure provided with at least one entry means through which users and/or materials enter the containment enclosure and at least one exit means through which users and/or materials exit the containment enclosure, said entry means and exit means are movable between a closed position and an open position. The containment enclosure comprises at least one production unit comprising at least one bioreactor for culturing the cells or virus, said bioreactor is provided with at least one inlet and at least one outlet and at least one purification unit fluidly connected to the production unit and comprising at least one purification device. The system is further provided with at least one inactivation (4) and/or at least one gas decontamination unit (6), positioned inside or outside the containment enclosure. The containment enclosure further comprises at least one process control device which collects, monitors and/or records data on actions performed by the units of said system.

By performing all the process and production steps in an enclosed containment, the safety risks for the environment linked to these steps are highly reduced. The provision of a process control device which acts as an ultimate gatekeeper of the system processes again greatly reduces any safety risk which might occur.

In a further embodiment, the process control device is able to control the access of said containment enclosure, preferably by controlling the movement of said exit means from a closed position to an open position connected to the at least one exit means whereby the movement of the exit means from the closed position to the open position is controllable by the process control device. In a further embodiment, access to the containment enclosure is only allowed once the process control device has received information on the completion of said inactivation and/or gas decontamination. It will be understood that this greatly reduces the risk of contaminating the environment outside the enclosed containment, and is thus an important safety measure. Especially when it comes to the production of viruses or viral particles of category BL3 where leakage of viral product is absolutely prohibited, this is particularly useful.

In a second aspect, the present invention provides a method for the production of cells, viruses or cells- or virus-derived products in a containment enclosure according to claim 18.

The system and/or the method of the present invention provide high a containment level and ensure prevention of environment contamination. By preference, the opening of the system's exit means is only allowed by the process control device when one or more predetermined actions is performed. This provides the user with a tool to control the completion of different steps of the process. The user can select the predetermined actions and can hence have a control on the completion of the steps leading to the production of the product of interest and/or the completion of the steps required for the decontamination and/or the sterilization of any material used during said production. The system according to the invention can be operated in class C or D clean room while providing the required biosafety level which is offered by the containment enclosure itself.

The systems and methods of the invention also allow rapid production of cells and/or cell products using significantly smaller equipment compared to the prior art systems and methods. Another advantage is to provide for high yield of cells and/or cell products compared to the methods and the systems of the prior art thereby reducing costs of the final product. The present invention provides cheaper fully-automated and integrated systems, which cost is at least 5 to 6 times less than the usual large-scale set-up systems. This eventually results in a lower investment and production cost, which is a considerable advantage.

The system of the invention is an integrated system which is provided with the required devices for all production steps and decontamination of the circulating air and/or liquids and/or solid materials. Additionally, the steps of the method of the invention can be performed in a subsequent manner in the containment enclosure and can be fully automated. Consequently, the system and the method of the invention considerably reduce operational effort and personnel intervention.

DETAILED DESCRIPTION OF THE INVENTION

The present invention concerns a system and a method for the production of biologics. In particular, the invention provides a system and a method for the production of cells, viruses or cells- or virus-derived products. Said cells, viruses or cells- or virus-derived products are herein referred to by "product" or "end-product".

Unless otherwise defined, all terms used in disclosing the invention, including technical and scientific terms, have the meaning as commonly understood by one of ordinary skill in the art to which this invention belongs. By means of further guidance, term definitions are included to better appreciate the teaching of the present invention.

As used herein, the following terms have the following meanings:

"A", "an", and "the" as used herein refers to both singular and plural referents unless the context clearly dictates otherwise. By way of example, "a compartment" refers to one or more than one compartment.

"About" as used herein referring to a measurable value such as a parameter, an amount, a temporal duration, and the like, is meant to encompass variations of +/−20% or less, preferably +/−10% or less, more preferably +/−5% or less, even more preferably +/−1% or less, and still more preferably +/−0.1% or less of and from the specified value, in so far such variations are appropriate to perform in the disclosed invention. However, it is to be understood that the value to which the modifier "about" refers is itself also specifically disclosed.

"Comprise," "comprising," and "comprises" and "comprised of" as used herein are synonymous with "include", "including", "includes" or "contain", "containing", "contains" and are inclusive or open-ended terms that specifies the presence of what follows e.g. component and do not exclude or preclude the presence of additional, non-recited components, features, element, members, steps, known in the art or disclosed therein.

The recitation of numerical ranges by endpoints includes all numbers and fractions subsumed within that range, as well as the recited endpoints.

Figure 1:
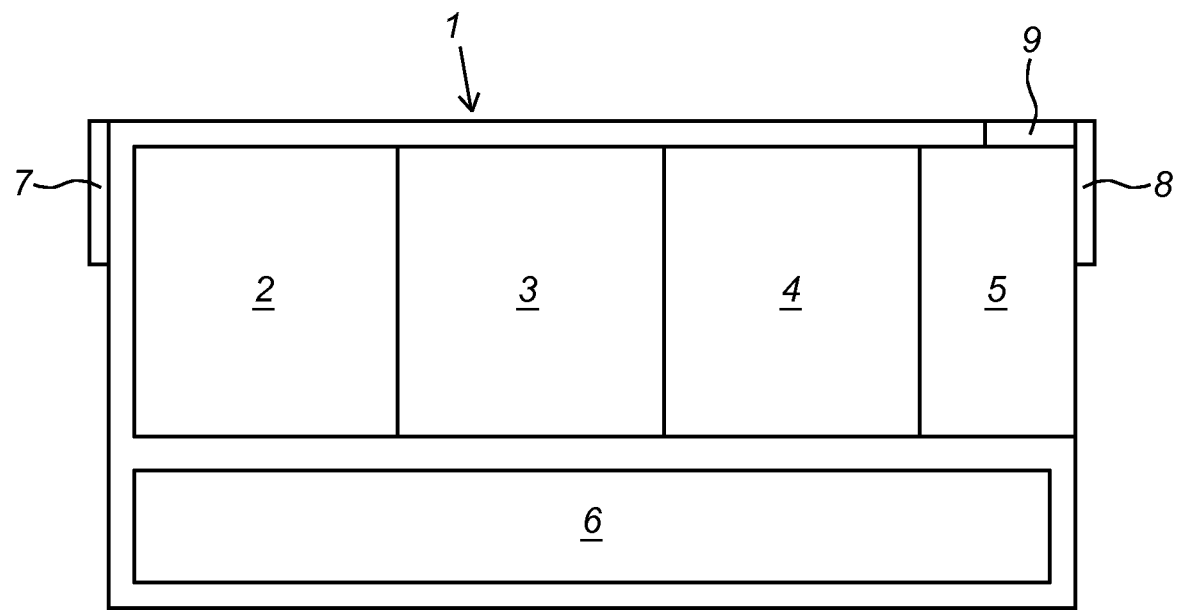
FIG. 1 shows an embodiment of the system wherein the containment enclosure comprises one inactivation unit.

In a first aspect, the present invention provides a system for the production of cells, viruses or cells- or virus-derived products. The system comprises a containment enclosure 1 having walls which define an enclosure inner space and an enclosure outer space. The inner space is configured to provide an aseptic environment for manufacturing production, purification and/or sterile fill and finish of the product. In an embodiment, the enclosure 1 is provided with at least one entry means 7 through which users and/or materials enter the containment enclosure and at least one exit means 8 through which users and/or materials exit the containment enclosure 1 (FIG. 1). In another embodiment, said entrance 7 and exit 8 means are the same and allow entering and exiting the enclosure via the same door or closable opening.

The entry means and exit means are movable between a closed position in which the enclosure inner space in not accessible and an open position in which the enclosure inner space in accessible to users and/or materials. Preferably the enclosure comprises at least one liquid material entry means and/or at least one solid material entry means and/or at least one user entry means. The enclosure also comprises at least one liquid material exit means and/or at least one solid material exit means and/or at least one user exit means.

The containment enclosure 1 comprises at least one production unit 2 comprising at least one bioreactor for culturing the cells or virus, said bioreactor is provided with at least one inlet and at least one outlet; at least one purification unit 3 fluidly connected to the production unit 2 and comprising at least one purification device, and at least one sterilization unit 5 fluidly connected any unit of the containment enclosure 1.

The units of the system which are comprised in the containment enclosure 1 might be separated from each other by sidewalls. Each unit might share at least one common wall with at least another unit of the system. Said common walls are provided with at least one access door for the passage of users and/or materials. In a further embodiment, any access door and/or any entry means 7 and/or any exit means 8 of the system is provided with an air-lock system that filters dust, particulate, and other contaminants from the air.

The access doors of the common walls and/or the entry means 7 and/or the exit means 8 can be made from a strong material, for example, aluminum, stainless steel, fiber glass or any other suitable material. The doors and/or the entry means 7 and/or the exit means 8 can include lift gate type doors, swing doors, shutters or sliding doors, and can include glass or Plexiglas panels. A suitable access mechanism, for example, a lock and key mechanism, a pass code punch pad, card swipe, transponder reader, finger print scanner, retina scanner, sensors, automatic identification and data capture methods such as radio-frequency identification (RFID), biometrics (like iris and facial recognition system), magnetic stripes, Optical character recognition (OCR), smart cards and voice recognition, or any other access mechanism, can be provided to unlock the doors and/or the entry means 7 and/or the exit means 8.

The system is further comprised of at least one inactivation unit (4) and/or at least one gas decontamination unit (6), which may be positioned either inside or outside the containment enclosure. These units will be able to inactivate any leftover viruses or viral particles in the system (e.g. tubings) once the production cycle is completed. The gas decontamination unit will be able to decontaminate all external surfaces and/or the air within the enclosed containment 1.

The containment enclosure 1 further comprises at least one process control device 9 which is able to collect, monitor and/or record data on actions performed by the units of said system. In one embodiment, the process control device 9 comprises a computer or one or more central processing units (CPUs) which generate input specific output signals. The input signals for the processing units are dependent on the processes taking place in the enclosure containment. The process control device's input data can be registered automatically using sensors, for instance, or manually by an operator.

In a further embodiment, said process control device 9 is able to control the access of said containment enclosure 1, preferably by controlling the movement of said exit means 8 from a closed position to an open position.

To that purpose, said process control device (9) may be connected to said entrance 7 and exit means 8 whereby the movement of the exit means from the closed position to the open position is controllable by the process control device 9. Said process control device 9 comprises at least one data input system through which information on the completion of a predetermined number of actions is entered and/or recorded in the process control device 9.

The predetermined number of actions comprises at least one of the following: status of the cell and/or virus culture, status of the purification of the product, status of liquid waste decontamination, status of solid material sterilization, status of product inactivation, status of gas decontamination. The status of said actions comprises: in progress, not started or completed. In a further embodiment, the opening of the exit means is allowed by the process control device 9 only when the status of all predetermined number of actions is entered as completed in the data input system. By preference, the process control device (9) is programmed to provide access to said containment enclosure 1, once said process control device (9) has received information on the status of said inactivation and/or gas decontamination.

This is advantageous as it provides controlled opening of the exit means thereby ensuring all actions and especially the inactivation of the virus and decontamination of the environment are completed. The risk of contamination of the external environment by the grown virus and/or cell is hence avoided.

The status of the predetermined action can be entered manually or automatically into the data input system of the process control device 9. The different devices of the units of the system might be provided with sensors which transfer the information on the predetermined number of actions to the data input system. Said transfer of information might be continuous or discontinuous. Preferably, the predetermined number of actions is defined by the user and is selected according to the product to be obtained and the liquid and/or solid material used for the production of said product.

In a further embodiment, at least one temperature is maintained in the different units of the containment enclosure 1. Said units of the enclosure and the enclosure itself might operate at similar or different temperatures. Preferably, the operating temperature of the production unit is between 20° C. and 40° C., more by preference between 25° C. and 37° C. The operating temperature of the purification unit is between 0° C. and 25° C., more preferably between 1° C. and 20° C., even more preferably between 2° C. and 10° C., most preferably about 4° C. The temperature of both units is maintained by cooling and/or warming units and maintenance of the temperature may be checked by sensors.

In another embodiment, the process control device 9 controls the cell or virus culture and/or purification and/or inactivation and/or decontamination processes, and is connectable to at least one unit of the containment enclosure. The process control device is configured to control the operations of any unit of the system. And can include a plurality of sensors, a local computer, a local server, a remote computer, a remote server, or a network. The process control device can be operational to control all aspects of the product manufacturing process, and can be coupled to sensors disposed in the bioreactor, for example, to control the temperature, volume flow rate and gas flow rate into the bioreactor in real time. The functioning controller can include a display, for example, a computer monitor, a smart phone app, a tablet app, or an analog display, that can be accessed by a user to determine the state of any unit of the system. The process control device can include an input, for example, a keyboard, a key pad, a mouse, or a touch screen, to allow a user to enter control parameters for controlling the operation of the any unit of the system.

In another embodiment, the pressure inside the containment enclosure when in closed configuration will be lower than the pressure outside said containment. In a further embodiment, said pressure will be 15 to 30 Pa less than the pressure outside the enclosure. This again lowers the risk for contaminations spreading to the outer environment. In a further embodiment, a ventilation system within the enclosed containment will be responsible for the negative air pressure in the enclosed containment once the entrance and/or exit is closed.

Production Unit

The production unit 2 comprises at least one bioreactor and at least one supply system such as tubings for supplying said bioreactor with cell medium and gas or gaseous mixture. The production unit might further comprise a tank comprising cell medium that can be introduced in the bioreactor. The bioreactor may be permanently or temporarily fixed to the production unit and might be reusable or a single use bioreactor.

In a further embodiment, the bioreactor allows high density cell growth. Said density is of at least 20 million cells/ml, preferably at least 40 million cells/ml, more preferably at least 60 million cells/ml, most preferably at least 100 million cells/ml. Said density can reach 300, 250 or 200 million cells/ml.

In another further embodiment, the bioreactor total volume is at least 1 L, preferably at least 10 L, more preferably at least 30 L, even more preferably at least 40 L, most preferably at least 50 L. The bioreactor total volume is at most 2500 L, preferably at most 200 L, more preferably at most 150 L, even more preferably at most 100 L, most preferably 75 L. By bioreactor total volume reference is made to the total liquid volume that can be introduced in the bioreactor, which will then be full. The bioreactor total volume and the bioreactor itself according to the invention are smaller compared to the conventional bioreactors used for high cell density culture. This is advantageous in terms of required space for the system and for ease of use.

The bioreactor can be any type of bioreactor that allows high cell density cultures. The bioreactor might be a perfusion bioreactor, wave bioreactor, cylindrical bioreactor, bag bioreactor, moving bed bioreactor, packed bed bioreactor, fibrous bioreactor, membrane bioreactor, batch bioreactor, or continuous bioreactor. The bioreactors can be made from a suitable material, for example, stainless steel, glass, or plastic. The bioreactors can include one or more sensors, for example, a temperature sensor (e.g., a thermocouple), flow rate sensor, gas sensor, or any other sensor.

The bioreactor might be provided with carriers such as fibers, microfibers, hollow fibers or hollow microfibers. Said carriers provide for an excellent substrate for the cells to grow on. In one embodiment, the bioreactor comprises carriers, by preference polyester microfiber carriers. In a further embodiment, the microfiber carriers are biocompatible. By preference, they are nonwoven polyester carriers. Following bioreactor inoculation with cells, the cell culture unit follows pre-programmed and automated processes to deliver culture media to the bioreactor and/or maintain pH and/or maintain temperature. Standard or unique cell culture growth parameters can be programmed, such that, various cell types can be expanded and such that cells or cell products can be harvested in an efficient, reproducible manner with minimal chance of human error. In a further embodiment, said carriers have received a plasma treatment in order to make them hydrophilic. The cells will attach to the carriers as a 3D growth substrate.

In another further embodiment, the carriers present in the bioreactor provide a cell growth surface of at least 0.5 square meters ($m^2$), at least 1 $m^2$, at least 5 $m^2$, at least 10 $m^2$, at least 20 $m^2$, at least 30 $m^2$, at least 40 $m^2$, at least 50 $m^2$, at least 60 $m^2$, at least 70 $m^2$, at least 80 $m^2$, at least 90 $m^2$, at least 100 $m^2$, at least 200 $m^2$, at least 300 $m^2$, at least 400 $m^2$. The carriers provide a cell growth surface of at most 2000 $m^2$, at most 1000 $m^2$, at most 800 $m^2$, at most 600 $m^2$ or any value comprised between the aforementioned values. Preferably, the cell growth surface provided by the carriers is about 500 $m^2$.

When the bioreactor is operated in perfusion mode or is a perfusion bioreactor, the ratio between the culture medium volume introduced in the bioreactor and the cell growth surface is at least 0.2 ml/$cm^2$, preferably at least 0.5 ml/$cm^2$. Said ratio allows introducing volumes of about 10 L in a bioreactor having cell growth surface of about 1 $m^2$, about 2500 L in a bioreactor having cell growth surface of about 500 $m^2$, and about 10000 L in a bioreactor having cell growth surface of about 2000 $m^2$ In another embodiment, the bioreactor is a small size bioreactor which can be of a circular shape having a diameter of at least 20 cm, preferably at least 40 cm and at most 100 cm, preferably at most 75 cm, more preferably at most 50 cm. Said bioreactor can also be a rectangular or square bioreactor having a height of least 40 cm, preferably at least 50 cm, more preferably at least 60 cm and at most 110 cm, preferably at most 100 cm, more preferably at most 80 cm, most preferably at most 70 cm. The width of said rectangular or square bioreactor is least 40 cm, preferably at least 50 cm, more preferably at least 60 cm and at most 100 cm, preferably at most 90 cm, more preferably at most 80 cm, most preferably at most 70 cm.

The bioreactor can be gyrated or motioned thereby increasing oxygen transfer and ensuring gas equilibrium in said bioreactor. This allows to run cultures in a bioreactor which is devoid of sensors thereby providing a simple and less complicated bioreactor installation compared to the bioreactors of the prior art. In addition, the use of a bioreactor devoid of sensors provides for a considerable decrease of contamination risk. Motioning the bioreactor further improves cells harvesting. Indeed, harvesting cells from a carriers-containing bioreactor, such as fibers or microfibers bioreactors has been difficult to accomplish. Typically, cells are sticky and attach themselves to the carriers or to other cells and form clusters. Motioning the bioreactor forces the cells free thereby providing increased efficiency of cell harvest at high cell viabilities without the use of chemical or enzymatic release additives. The bioreactor may have a rigid or a non-rigid outer body. Rigid outer body allows for the bioreactor case to be flexed causing microfiber movement. This movement enhances the release of cells that have attached to the side of the bioreactor matrix.

In one embodiment, the bioreactor is provided with at least one inlet for the introduction of gas and/or culture medium and at least one outlet for the collection of the medium contained in the bioreactor. At least one in-tubing is provided for fluidly connecting the bioreactor, via its inlet, to a culture medium tank and/or a gaseous source. At least one out-tubing is provided for fluidly connecting the bioreactor, via its outlet, to the purification unit or any device of said unit. The bioreactor might be provided with at least one internal filter.

In a further embodiment, the culture medium is introduced in the bioreactor using at least one pump. By preference, the medium is pre-heated to a temperature of between 25° C. to 37° C. and mixed prior to transfer to the bioreactor. This ensures that the cells will not perceive a cold-shock when being contacted with new medium (which would negatively affect their growth) as well as ensure that all nutrients in the medium are mixed and present in the required amounts. The medium can be a liquid comprising a well-defined mixture of salts, amino acids, vitamins and one or more protein growth factors.

Gas such as pure oxygen or a gaseous mixture comprising oxygen is equally provided through the bioreactor inlet. Oxygen is an essential requirement for the normal growth of mammalian cells. By preference, said gas or gaseous mixture is supplied under pressure. In an embodiment, cells will be exposed to dissolved oxygen concentrations of 300 μM or less (160 mmHg partial pressure), by preference less than 200 μM, most preferably between 20 and 150 μM.

In a further embodiment, gas or gaseous mixture and culture medium will be intermixed prior being supplied to the bioreactor. Hence, the mix of gas or gaseous mixture and culture medium are supplied to through one supply line. This gives as an advantage that a cell medium with optimal oxygen concentration is provided directly to the cells. In another further embodiment, said gas or gaseous mixture is chosen from air or oxygen. By preference, air is being used. Air is to be seen as a gaseous mixture, comprising approximately 78% of nitrogen, 21% of oxygen and argon and carbon dioxide. Supply of air instead of pure oxygen or oxygen enriched atmospheres has as an advantage that the system employing the method can be omitted of supplying units of highly concentrated oxygen, which may otherwise imply a fire or explosion hazard.

The low solubility of oxygen in aqueous medium (such as a cell culture medium) relative to its rate of consumption causes its rate of supply to be the limiting factor for cell growth. Generally, the oxygen transfer rate in a fermentor or bioreactor is described by:

$$OTR = KLa(C_{gas} - C_{liq}),$$

Whereby OTR=oxygen transfer rate in μmol O2 $l^{-1}$ $h^{-1}$;
KLa=is the oxygen transfer coefficient in $h^{-1}$;
$C_{liq}$=gas-phase O2 (equilibrium) concentration in μM;
$C_{liq}$=liquid phase O2 concentration in μM By preference, the oxygen transfer coefficient (KLa) in the current method is at least 20 $h^{-1}$, preferably at least 30 $h^{-1}$, more preferably at least 35 $h^{-1}$. Said oxygen transfer coefficient is at most 100 $h^{-1}$, preferably at most 50 $h^{-1}$, more preferably at most 40 $h^{-1}$.

A high oxygen transfer coefficient and therefore also high OTR will have a positive influence on the cell growth/health and hence the yield of the desired end product. It was found by the inventors of the current method that an oxygen transfer coefficient as defined above is particularly beneficial in terms of product yield, even when making use of a rather small amount of cell starter culture.

Purification Unit

Figure 3:
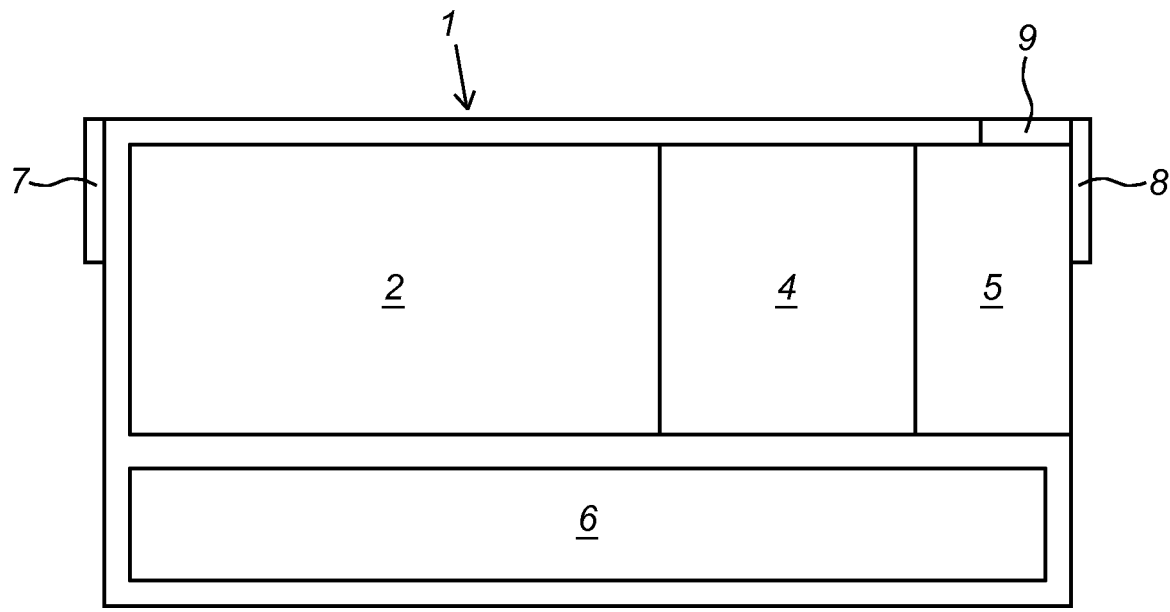
FIG. 3 shows an embodiment of the system wherein the production unit and the purification unit are comprised in a single room inside the containment enclosure.

The purification unit 3 might be separate from and is preferably sharing a common wall with the production unit. Said common wall preferably comprises at least one door through which users and/or material can pass. The purification unit might also be positioned in the same room 2 as the purification unit (FIG. 3). In this configuration a single room comprises a first working space or bench which is the production unit and a second working space or bench which is the purification unit.

The purification unit 3 comprises at least one purification device which is provided with an inlet and an outlet. The inlet is fluidly connected to the outlet of the bioreactor. Said purification device is selected from the group comprising a filtration device, an ultrafiltration device, a diafiltration device, a pH adjustment device, a centrifugation device, a washing device, a chromatography column, a chromatography membrane, a harvest device, a dialysis device, a concentration device or any combination thereof. Each of said devices is provided with at least one inlet and one outlet allowing the device to be connected to any other device of the same unit or of a different unit of the system.

In another embodiment, a filtering device is provided in the containment enclosure. The filter will selectively retain molecules based on their mass in Dalton for instance. The filtering device may comprise virus hollow filters with might be used to filter and remove virus particles from the solution flowing out of the bioreactor.

The chromatography column might be an affinity chromatography, ionic exchange chromatography (e.g. anion or cation), hydrophobic interaction chromatography, size exclusion chromatography (SEC), immuno-affinity chromatography which is a column packed with an affinity resin, such as an anti-IgM resin, a Protein A, a Protein G, or an anti-IgG resin. The size of the chromatography column may vary based on the type of product to be purified and/or the volume of the solution from which said product is to be purified. In a further embodiment, the purification device is fluidly connected to at least one source of eluting solution for eluting and recuperating the molecule of interest.

In a further embodiment, the production unit and/or the purification unit and/or any device of said units is fluidly connected to a liquid waste container which can be positioned inside or outside the containment enclosure. Any other unit or device of the enclosure might also be fluidly connected to the liquid waste container. Necessary connections and devices are provided for diverting the liquid waste from the bioreactor and/or any device of the system to the waste container.

In another embodiment, the system comprises at least one waste decontamination device which is positioned inside the containment enclosure 1 for decontamination of any liquid waste, said waste decontamination device is positioned upstream and/or downstream the liquid waste container. The waste decontamination device might be a heating device which heats the liquid waste to a temperature sufficient for inactivation of all viruses and/or cells present in said liquid waste. This is advantageous as it ensures that any liquid waste flowing out of the containment enclosure is decontaminated and free of any active virus and/or cells. Contamination of the external environment of the enclosure is thereby avoided and effective containment during the production of the product is provided.

Inactivation Unit

In another embodiment, the inactivation unit 4 contains at least one virus inactivation means; said inactivation unit is connectable to any unit of the containment enclosure 1. The inactivation compositions are selected from the group comprising formaldehyde, at least one detergent, at least one acid or any combination thereof. Other inactivation compositions may comprise a potassium persulphate solution (commercially known as Virkon®), sodium hydroxide or bleach.

Figure 4:
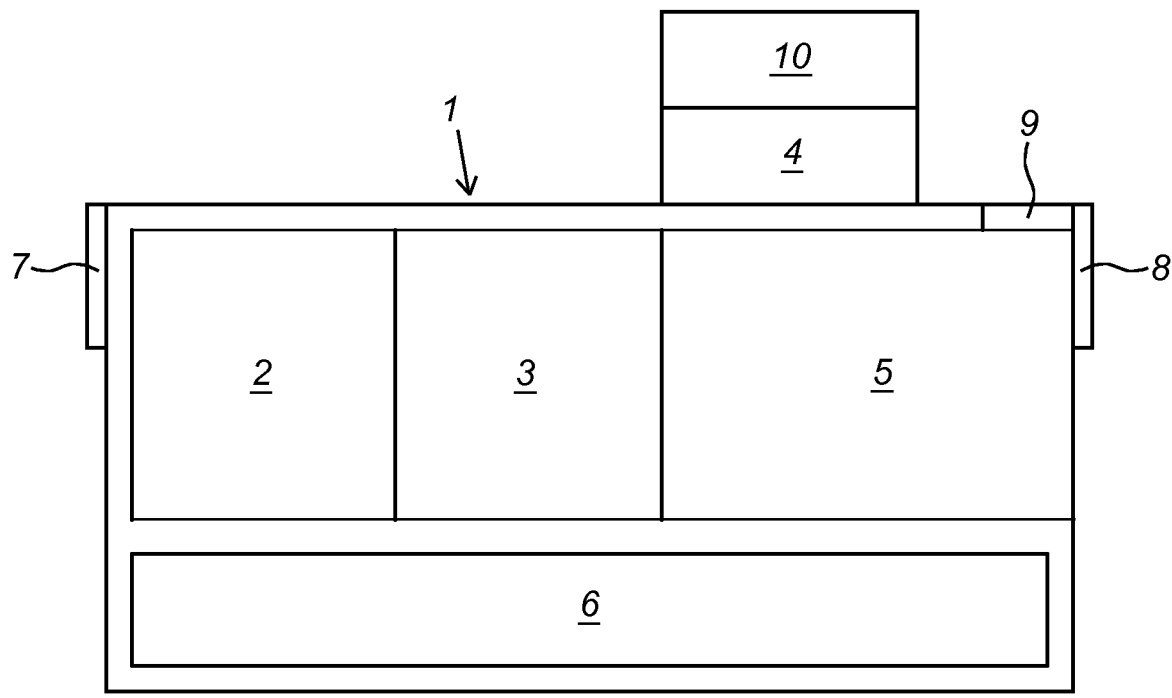
FIG. 4 shows an embodiment of the system wherein the containment enclosure is connected to an inactivation unit and a fill and finish unit both positioned outside the containment enclosure.

The inactivation unit 4 might be positioned inside or outside the containment enclosure 1 (FIG. 4). When positioned inside the enclosure, the inactivation unit is preferably separated from and shares a common wall with the production unit and/or the purification unit and/or the room comprising the production unit and the purification unit. Said common wall preferably comprises at least one door through which users and/or material can pass.

In a further embodiment, the solution obtained from the purification device is supplemented with an amount of an inactivation composition, preferably formaldehyde, which is sufficient to inactivate the cells and/or viruses present in said solution. Formaldehyde is preferably used as a 37 wt % solution and is added to the solution obtained from the purification device such that the formaldehyde concentration in said solution is at least 0.005%, preferably at least 0.01%, more preferably at least 0.02%, most preferably 0.03% and at most 0.1%, preferably at most 0.08%, more preferably at most 0.06%. The inactivation is preferably carried out at constant temperature which is at least 30° C., preferably at least 35° C., more preferably about 37° C.

In a further embodiment, prior to the inactivation, a filtration of the solution obtained from the purification unit is performed. A filter having a pores size of at least 0.1 mm, preferably at least 0.2 mm and at most 1 mm, preferably at most 0.8 mm is used. The filtration allows removal of cells or viruses aggregates thereby better exposing cells and/or viruses to formaldehyde.

Figure 2:
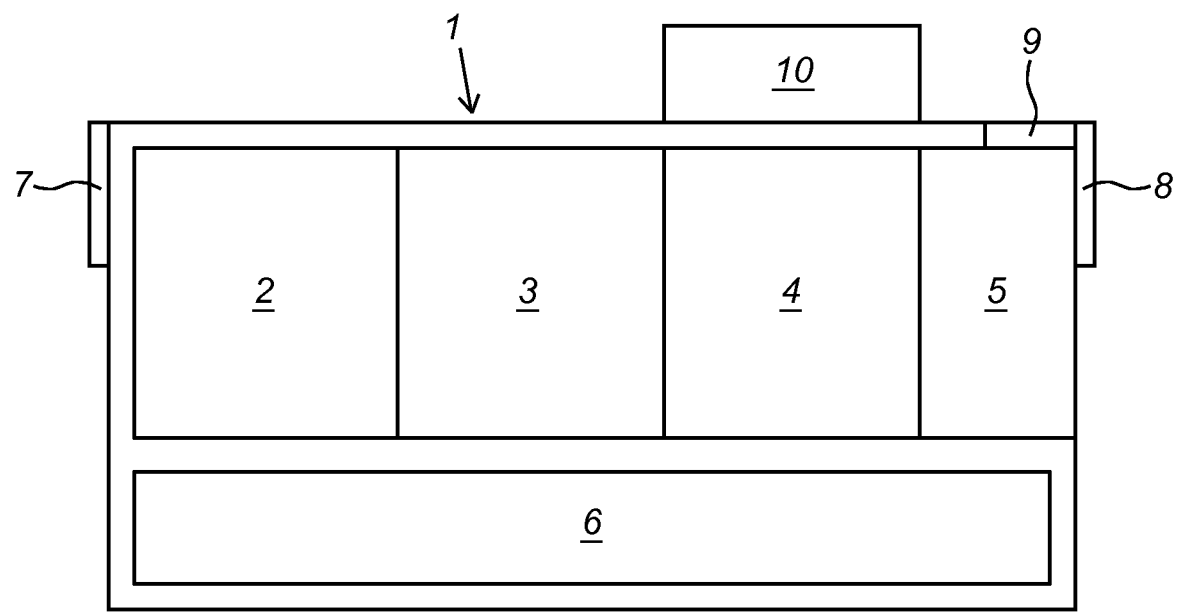
FIG. 2 shows an embodiment of the system wherein the containment enclosure is connected to a fill and finish unit positioned outside the enclosure.

The inactivated solution is then transferred to a fill and finish unit 10 (FIG. 2) which might be positioned inside the inactivation unit. Said fill and finish unit 10 might also be positioned outside the containment enclosure 1 of the system.

The fill and finish unit 10 might be separate from the inactivation unit and shares a common wall with it. Said common wall preferably comprises a door. In the fill and finish unit, the inactivated solution undergoes any or any combination of the following steps: concentration, packaging sterilization. The person skilled in the art recognizes that the fill and finish unit comprises utility suitable for performing any of the mentioned steps. Said utility comprise vials, bottles, syringes, pumps, lyophilization equipment, cap/stopper equipment, final packaging/wrapping equipment and any other packaging equipment or combination thereof.

Figure 5:
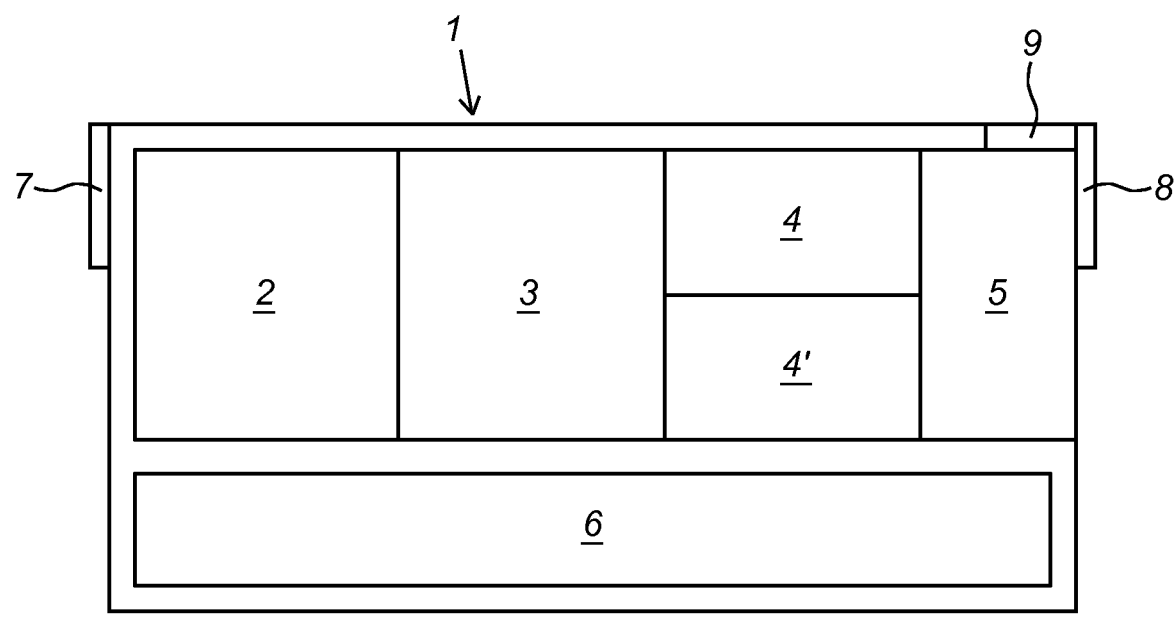
FIG. 5 shows an embodiment of the system of the invention wherein the containment enclosure comprises two inactivation units.

The system might comprise more than one inactivation unit with intermittent functioning. This allows initiation of a second cell or virus culture while the first solution obtained from a first culture is being inactivated. For instance, with reference to FIG. 5, a first cell or virus culture is initiated in the production unit 2, the culture solution is then purified in the purification unit 3, the purified solution is inactivated in a first inactivation unit 4. While inactivation process in ongoing, a second cycle of cell or virus culture is initiated in the production unit 2, the second culture solution is then purified in the purification unit 3 and inactivated in a second inactivation unit 4'. While the second purified solution is being inactivated in the second inactivation unit 4', the first inactivation unit 4 is sterilized and ready for the inactivation of a solution derived from a third cell or virus culture. This is advantageous as it optimizes the use of the system and leads to the production of high rates in a short time compared to the systems of the prior art.

Gas Decontamination Unit

The gas decontamination unit 6 is preferably fluidly connected to any unit of the containment enclosure 1, said gas decontamination unit comprises at least one gas decontamination means which is selected from the group comprising hydrogen peroxide, aerosol, formaldehyde vaporizing device, hydrogen peroxide vaporizing device, aerosol vaporizing device or any combination thereof. The gas decontamination unit 6 might operate in continuous or discontinuous mode during the full process of the production of the product. The gas decontamination unit 6 allows decontamination of air circulating in and all surfaces of the enclosure and its different units. The gas decontamination unit 6 might be positioned inside or outside the containment enclosure 1.

The gas decontamination means 6 might include an HVAC system configured to provide hot and/or cool air to the inner space of the enclosure 1, and/or provide humidity control. Preferably said HVAC system includes at least one filter to purify the air coming into the inner space. For example, HEPA filters can be included to provide a controlled amount of particulate flow to the internal volume defined by the enclosure 1. In another embodiment, decontamination may occur via the provision of a heated air flow, whereby the temperature of the air flow is preferably above 70° C.

Sterilization Unit

The system may optionally comprise a sterilization unit 5 which may comprise at least one autoclave for sterilization of any solid material used during the production of the product. Said solid material includes bottles, vials and pipets.

The sterilization unit can comprise a weight measurement device for measuring the weight of the sterilized solid material. In a further embodiment, the status of solid sterilization mentioned above comprises a predetermined weight of solid material that should be sterilized.

In a second aspect, the invention provides a method for the production of cells, viruses or cells- or virus-derived products in a containment enclosure 1. Preferably, said containment enclosure is an enclosure as described above or any other containment enclosure which is able of performing the essential steps of the method.

More specifically, said containment enclosure is closed off from the surroundings during its operation. Said production in said containment enclosure (1) comprises the growth of said cells and/or viruses in a bioreactor and subsequently purifying said cells, viruses or products derived thereof in a purification unit which is in fluid connection with said bioreactor, and wherein after production of the end-product said containment disclosure and units within are decontaminated and any remaining viral or cellular particles in the units except from the desired end product are inactivated, wherein the actions during the production process and decontamination and inactivation procedure are monitored and/or controlled by a process control device present in said system.

In one embodiment, the access to the containment enclosure after a production cycle has occurred is controlled by the process control device. More specifically, said process control device allows entrance to the containment enclosure once it has registered, recorded and/or retrieved information about the finalization of the decontamination and inactivation process within said system.

In another embodiment, said enclosure containment is provided with at least one entry means 7 through which users and/or materials enter the containment enclosure and at least one exit means 8 through which users and/or materials exit the containment enclosure 1, said entry means and exit means are movable between a closed position and an open position. The method of the invention further comprises the following steps:

culturing the cells or virus in at least one bioreactor which is positioned in a production unit 2 comprised in the containment enclosure 1, purifying the cells, virus and/or the virus product in a purification unit 3 which is comprised in the containment enclosure 1 and is fluidly connected to the bioreactor of the production unit 2, decontaminating said containment enclosure and/or at least one unit of said enclosure and inactivating cells, virus and/or the virus product and moving the exit means 8 from the closed position to the open position such that users and/or materials can exit the containment enclosure 1, whereby the movement of the exit means (8) is controlled by a process control device (9) comprised in the containment enclosure (1) once said process control device learns that said decontamination and inactivation has finalized.

Communication between the process control device (9) and the exit means (8) and/or entrance means of the containment enclosure occurs via conventional methods and systems known in the art, for instance a signal generated by a sensor is transmitted to the processing unit of the process control device. In another embodiment the signal can be converted before transmission to the process control device.

The bioreactor and the different units of the method are preferably as described above.

In another embodiment, the method further comprises the step of entering data relative to the completion of a predetermined number of actions into a data input device comprised in the process control device 9 for moving said exit means from the closed position to the open position. The exit means are only moved from the closed position to the open position only when data indicating that all predetermined actions are in a completed status. The actions and their status are as described above. The data on the status of the predetermined actions might be automatically or manually entered into the data input device of the process control device 9.

The step of inactivating the cells and/or the virus or viral particles (except the end product) preferably occurs in a virus inactivation unit 4 which is connectable to the containment enclosure 1. The inactivation unit comprises at least one inactivation composition. The inactivation unit and the inactivation composition are as described above.

Decontaminating the containment enclosure 1 and/or at least one unit of said enclosure is performed by a gas decontamination unit 6 which is fluidly connected to the enclosure and/or any unit of said enclosure 1. The gas decontamination unit is as described above.

In a further embodiment, the method comprises the step of decontaminating any liquid waste inside the containment enclosure 1 prior to directing said liquid waste to a liquid waste container. The decontamination of liquid waste is carried out by at least one waste decontamination composition. The liquid waste container and the waste decontamination composition are as described above. The liquid waste container is fluidly connected to any device and/or unit of the system. The liquid waste might be directed to the liquid waste container in continuous or discontinuous mode.

Preferably, the method of the invention is performed in a system according to any embodiment of the invention. Preferably, where applicable, any embodiments of the system apply to the method and vice versa.

The person skilled in the art will appreciate that necessary tubing and/or pump can be provided within the system for achieving the fluid connection between the different units and/or the different devices. Further, the system can be provided with a plurality of switch valves used to route the fluids between said different units and/or devices. In addition, a software program for running the system and the method according to an embodiment of the invention can be provided.

While the system and method as described above can be used to produce biomolecules or products derived of any kind of organism or pathogen (e.g. virus), regardless of the safety risk associated to said organism or pathogen, it will be understood that it is especially beneficial for those pathogens which are labeled to be of a higher risk, such as biosafety level 3 and 4. Without being understood as limitative, the system and method according to the current invention is particularly useful for production of viral particles (or products derived thereof) of poliovirus, Venezuelan equine encephalitis virus, Eastern equine encephalitis virus, Western equine encephalomyelitis (WEE) virus, SARS coronavirus, Rift Valley fever virus, Central European tick-borne encephalitis, chikungunya, yellow fever virus, West Nile virus, Marburg virus, Ebola virus, Lassa virus, Crimean-Congo hemorrhagic fever, Hendra virus, Nipah virus, Variola virus.

In a further embodiment, the containment enclosure as described above may itself also be contained in containment unit, which encompasses the containment enclosure completely, thereby creating a box-in-a-box concept. As such an extra barrier around the production unit is created, again enhancing the safety of the system and methodology (especially when above mentioned organisms are being used). This containment unit could be a modular construction or structure around the containment enclosure. Said construction or structure can be provided with infrastructure or units necessary for assisting with the production of the biomolecules or products. For instance, said construction may comprise a controlled air, sealable, sterilisable cleanroom, supply and storage areas, laboratory equipment, an air conditioning system, connectors for air, gas and/or fluid supply, connectors for providing electricity, temperature control systems, pressure control systems etc. An example of a containment unit suitable for enclosing the containment enclosure as described in one of the embodiments above is disclosed in US20130109291.

In an embodiment, access to the first containment unit or rooms within said unit encompassing the containment enclosure can be controlled in a similar way as the access to the containment enclosure. The process device unit of the containment enclosure may communicate or be connected to the doors providing access to the containment unit or specific areas within, e.g. when the process control device has learned that the required steps such as decontamination and inactivation within the containment enclosure has taken place or that the production in the enclosure has occurred as scheduled and without any calamities. This may provide an additional safety barrier in case of problems.

In another embodiment, the containment unit itself may be provided by a process control device or a processor which registers actions performed by and/or within the containment unit or areas within said unit. Said process control device of the containment unit may decide upon the accessibility of the unit or areas within.

It is supposed that the present invention is not restricted to any form of realization described previously and that some modifications can be added to the presented example without reappraisal of the appended claims.

FIGURES

FIGS. 1 to 5 depict various configurations of a system and containment enclosure according to an embodiment of the current invention. Note that the sterilization unit (5) is optional in any of the shown embodiments. It will be understood that the embodiments shown in the figures are not to be understood as limitative for the current invention and that other embodiments may be encompassed by the claims as well.

The invention claimed is:

1. A system for the production of cells, viruses or cells- or virus-derived products, comprising a containment enclosure (1) provided with entry means (7) through which users or materials enter the containment enclosure and exit means (8) through which users or materials exit the containment enclosure (1), said entry means and exit means are movable between a closed position and an open position, wherein the containment enclosure (1) comprises:
   at least one production unit (2) comprising at least one bioreactor for culturing the cells or virus, said bioreactor is provided with at least one inlet and at least one outlet, and
   at least one gas decontamination unit (6), positioned inside or outside the containment enclosure, configured to perform gas decontamination of the containment enclosure,
wherein the containment enclosure (1) further comprises at least one process control device (9), wherein said at least one process control device (9) collects, monitors or records data on actions performed by the units of said system, wherein said at least one process control device (9) is programmed to cause the gas decontamination unit (6) to perform gas decontamination of the containment enclosure (1) upon completion of the culturing of the cells or virus by the at least one bioreactor and provide access to said containment enclosure (1) via the entry means (7) or exit means (8) upon receiving information on the completion of gas decontamination of the containment enclosure (1) by said gas decontamination unit.

2. The system according to claim 1, wherein the process control device (9) comprises at least one data input device through which information on the completion of a predetermined number of actions is entered or recorded in said process control device.

3. The system according to claim 1, characterized in that the process control device (9) is able to control the access of said containment enclosure (1), by controlling the movement of said exit means (8) from a closed position to an open position.

4. The system according to claim 1 further comprising a sterilization unit (5), wherein said sterilization unit (5) comprises at least one autoclave for sterilization of solid materials.

5. The system according to claim 1, wherein said gas decontamination unit (6) is connected to any unit of the containment enclosure (1), and comprises at least one gas decontamination means which is selected from the group comprising hydrogen peroxide, aerosol, formaldehyde vaporizing devices, hydrogen peroxide vaporizing devices, aerosol vaporizing devices or any combination thereof.

6. The system according to claim 1 wherein the bioreactor is fluidly connected to a liquid waste container.

7. The system according to claim 6 wherein the liquid waste container is positioned inside the containment enclosure.

8. The system according to claim 6 wherein the liquid waste container is positioned outside the containment enclosure.

9. The system according to claim 1, further comprising at least one waste decontamination device contained in the containment enclosure (1) for decontamination of any liquid waste, wherein said waste decontamination device is positioned upstream or downstream of a liquid waste container.

10. The system according to claim 1 wherein at least one temperature is maintained in the different units of the containment enclosure (1).

11. The system according to claim 1 further including a purification device provided with an inlet which is fluidly connected to the outlet of the bioreactor and is selected from the group comprising an ultrafiltration device, a diafiltration device, a centrifugation device, a washing device, a chromatography column or any combination thereof.

12. The system according to claim 1 wherein the process control device controls the cell or virus culture or inactivation or disinfection processes, and is connectable to at least one unit of the containment enclosure.

13. The system according to claim 1, wherein the entry (7) and exit means (8) are the same.

14. The system according to claim 1, characterized in that said containment enclosure (1) is enclosed by a containment unit.

15. The system of claim 1, wherein said gas decontamination unit (6) is connected to any unit of the containment enclosure (1), and comprises an HVAC system configured to provide hot or cool air to the inner space of the enclosure (1), wherein decontamination occurs via the provision of a heated air flow with a temperature above 70° C.

16. The system of claim 1, further comprising an inactivation unit (4), said inactivation unit (4) comprising at least one virus inactivation means, said virus inactivation means comprising an inactivation composition, characterized in that said inactivation unit is connectable to any unit of the containment enclosure.

* * * * *